(12) United States Patent
Auerbach (10) Patent No.: US 8,255,172 B2
(45) Date of Patent: Aug. 28, 2012

(54) WAFER DEFECT DETECTION SYSTEM AND METHOD

(75) Inventor: Ditza Auerbach, Aseret (IL)

(73) Assignee: Applied Materials Israel, Ltd., Rehovot (IL)

( * ) Notice: Subject to any disclaimer, the term of this patent is extended or adjusted under 35 U.S.C. 154(b) by 275 days.

(21) Appl. No.: 12/566,448

(22) Filed: Sep. 24, 2009

(65) Prior Publication Data

US 2010/0076699 A1    Mar. 25, 2010

Related U.S. Application Data

(60) Provisional application No. 61/099,812, filed on Sep. 24, 2008.

(51) Int. Cl.
*G06F 19/00* (2006.01)

(52) U.S. Cl. .......................................................... 702/35

(58) Field of Classification Search .................... 702/35, 702/182–185
See application file for complete search history.

(56) References Cited

U.S. PATENT DOCUMENTS

2009/0073440 A1 *    3/2009    Tiemeyer ..................... 356/338

* cited by examiner

*Primary Examiner* — Edward Raymond
(74) *Attorney, Agent, or Firm* — Tarek N. Fahmi, APC (57) ABSTRACT

Random defects and repeaters accommodated on a wafer are detected using slice information obtained by scanning a plurality of wafer slices; analyzing defect information using a first set of filters selected to detect random defects, thereby generating a first set of defects per slice, analyzing the defect information using a second set of filters selected to detect repeaters, thereby providing a second set of defects per slice; analyzing a plurality of the second sets of defects per slice using a third set of filters selected to detect repeater families, thereby providing a set of repeaters per wafer; and optionally combining the set of repeaters per wafer with a plurality of the first sets of defects per slice, thereby generating one or more defect maps indicative of random defects and/or repeaters.

22 Claims, 8 Drawing Sheets

WAFER DEFECT DETECTION SYSTEM AND METHOD

REFERENCE TO APPLICATIONS

Priority is claimed from U.S. provisional application No. 61/099,812, entitled "High Sensitivity Repeater Detection in Wafer Inspection", filed 24 Sep. 2008, incorporated herein by reference.

FIELD OF THE INVENTION

The present invention relates generally to wafer defect detection systems.

BACKGROUND OF THE INVENTION

Many wafer defect detection systems are known in the art.

The disclosures of all publications and patent documents mentioned in the specification, and of the publications and patent documents cited therein directly or indirectly, are hereby incorporated by reference.

SUMMARY OF THE INVENTION

Repeater Defects or "field repeaters" are systematic defects which appear at a specific location in a field. Field repeaters are often associated with mask problems, such as for example haze defects, as opposed to die-level systematic defects which are often associated with a marginal process. Conventionally, repeater analysis is carried out on the final result of inspection (a defect map) in order to identify the defects that are repeaters.

Certain embodiments of the present invention seek to provide a defect detection system in which Repeater defects are detected at a sensitivity which is much higher than inspection sensitivity in the same inspection scan.

Certain embodiments of the present invention seek to provide a defect detection system with enhanced purifying capabilities to filter "False Repeaters" i.e. repeaters which are not caused by mask faults.

Certain embodiments of the present invention seek to provide a defect detection system enabling high-sensitivity haze monitoring on inspected wafers.

Certain embodiments of the present invention seek to provide a defect detection system with no substantial throughput hit to a conventional inspection recipe.

Certain embodiments of the present invention seek to provide a defect detection system in which inspection images of the repeaters are available as output without any TPT hit.

According to certain embodiments, a high resolution (e.g. ⅓, ⅕ of the search radius characterizing the repeater analysis) field histogram is generated while scanning. Once a defect is placed in the histogram, the current numbers of its die to die (D2D) and field to field (F2F) occurrences are identified and if F2F>=Number of occurrences and (D2D−F2F)/F2F<Purifier Threshold, an image for this defect is fetched.

Occurrences are counted in a suitable vicinity, such as a 3×3 neighborhood, of a given bin in order to reduce sensitivity to the histogram discretization. Typically, the resolution of the field histogram is less than 1 micrometer and only coordinate attributes of these defects are saved in the histogram. A hash table may be used for memory saving using conventional techniques.

The cut-off point of the binarized histogram need not be 1 defect per vicinity vs. two or more. Any other suitable cut-off point may be employed such as 0-9 defects vs. 10 or more.

Suitable repeater filters typically separate haze defects from other process related repeater defects and may for example include:

A. Extent (Anti-crawling)-type repeater filters operative to filter out defect families which have a large extent; and/or B. Purifier-type repeater filters operative to filter out repeaters that typically occur much more often than once per field.

There is thus provided, in accordance with at least one embodiment of the present invention, a method for analyzing an object bearing a repeating pattern suffering from random defects which it is desired to find using a first sensitivity and first false alarm rate and from repeater defects which it is desired to find at a second sensitivity higher than the first sensitivity and second false alarm rate, the method comprising performing a single scan of at least a portion of interest within a object; using a first defect detection path to detect a first set of defects in the object thereby to generate a first defect map comprising a first plurality of defect locations; and using a second weaker defect detection path to detect a second set of defects in the object thereby to generate a second defect map comprising a second plurality of defect locations and generating a specific map by extracting a specific class of defects from the second set of defects, thereby to find on the object, defects not falling within the specific class, using only a single scan and using the first sensitivity, and also to find on the object, defects falling within the specific class, using the same scan but using the second sensitivity.

Further in accordance with at least one embodiment of the present invention, the specific map comprises a repeater map and the specific class of defects comprises repeater defects.

Still further in accordance with at least one embodiment of the present invention, the first and second paths include first and second filter cascades respectively and wherein the second filter cascade includes at least one filter having a lower threshold than a corresponding filter in the first filter cascade.

Still further in accordance with at least one embodiment of the present invention, the method also comprises pruning the repeater map to eliminate die-level systematic defects.

Additionally in accordance with at least one embodiment of the present invention, the pruning is performed after at least a substantial fraction of the portion of interest within the object has been scanned and wherein the pruning comprises retaining as repeater defects, only defect locations, each individual one of which share a field position with a number of other defect locations which number is at least almost as large as the number of defect locations which share a die position with the individual defect location.

Still further in accordance with at least one embodiment of the present invention, the substantial fraction of the object comprises the entirety of the object.

Additionally in accordance with at least one embodiment of the present invention, the method also comprises accumulating information regarding repetition of defects detected by the first detection path as the repetition is encountered and before the scan of the object has been completed; evaluating, per-slice, the information including using the information to generate a repeater analysis output and using the repeater analysis output to select for imaging, only a subset of defects detected by the first defect detection path; and, per-slice, requesting images only of the subset of defects detected by the first defect detection path.

Further in accordance with at least one embodiment of the present invention, the method also comprises merging at least some of the maps thereby to obtain a map of a predetermined logical combination of defects included in the maps.

Still further in accordance with at least one embodiment of the present invention, the object comprises a wafer.

Additionally in accordance with at least one embodiment of the present invention, the accumulating includes accumulating information regarding repetition of defects detected by the first detection path in an individual slice of the object as the slice of the object is being scanned and before scanning of the slice has been completed.

Also provided, in accordance with at least one embodiment of the present invention, is a method for detecting random defects and repeaters accommodated on a wafer, the method comprising performing defect detection on slice information provided by scanning a plurality of wafer slices, analyzing the defect information using a first set of filters selected to detect random defects, thereby generating a first set of defects per slice and analyzing the defect information using a second set of filters selected to detect repeaters, thereby providing a second set of defects per slice; analyzing a plurality of the second sets of defects per slice using a third set of filters selected to detect repeater families, thereby providing a set of repeaters per wafer; and combining the set of repeaters per wafer with a plurality of the first sets of defects per slice, thereby generating one or more defect maps indicative of the random defects and/or repeaters.

Further in accordance with at least one embodiment of the present invention, the method also comprises initiating, upon generating a first set of defects per slice, a request for images corresponding to defects included in the first set of defects per slice; and/or upon generating a second set of defects per slice, initiating a request for images corresponding to defects included in the second set of defects per slice, thereby enabling allocation of images associated with defects included in the defect map.

Still further in accordance with at least one embodiment of the present invention, the defect detection on slice information includes clustering of alarms included in the slice information into suspected defects by computation of volume, grade and type.

Further in accordance with at least one embodiment of the present invention, the first set of filters and the second set of filters have at least one filter in common; have a different number of filters, the second set of filters includes less filters than the first set of filters; and have at least one filter in common and the filter included in the second set of filters is configured with a lower threshold than a corresponding filter in the first set of filters.

Further in accordance with at least one embodiment of the present invention, at least one of the first set of filters and the second set of filters includes at least one of the following filters: Nuisance filter, GV filter, a defect level filter.

Additionally in accordance with at least one embodiment of the present invention, the third set of filters includes at least one of the following filters: Nuisance filter, GV filter, a defect level filter.

Further in accordance with at least one embodiment of the present invention, combining the set of repeaters per wafer with a plurality of the first sets of defects per slice includes one of the following: selecting defects included in both the set of repeaters per wafer and the plurality of the first sets of defects per slice; selecting defects included at least in the set of repeaters per wafer or the plurality of the first sets of defects per slice; and updating attributes associated with defects included in the first or second set with defect information included in the second or first set, respectively.

Still further in accordance with at least one embodiment of the present invention, the first and second paths include first and second filter cascades respectively and wherein the second filter cascade includes less filters than the first filter cascade.

Also provided, in accordance with at least one embodiment of the present invention, is a system for analyzing an object bearing a repeating pattern suffering from random defects which it is desired to find using a first sensitivity and first false alarm rate and from repeater defects which it is desired to find at a second sensitivity higher than the first sensitivity and second false alarm rate, the system comprising a scanner performing a single scan of at least a portion of interest within a object; a first detection functionality using a first defect detection path to detect a first set of defects in the object thereby to generate a first defect map comprising a first plurality of defect locations; and a second detection functionality using a second weaker defect detection path to detect a second set of defects in the object thereby to generate a second defect map comprising a second plurality of defect locations and generating a specific map by extracting a specific class of defects from the second set of defects, thereby to find on the object, defects not falling within the specific class, using only a single scan and using the first sensitivity, and also to find on the object, defects falling within the specific class, using the same scan but using the second sensitivity.

Also provided, in accordance with at least one embodiment of the present invention, is a system for detecting random defects and repeaters accommodated on a wafer, the system comprising a defect detector performing defect detection on slice information provided by scanning a plurality of wafer slices; a defect information analyzer analyzing the defect information using a first set of filters selected to detect random defects, thereby generating a first set of defects per slice, analyzing the defect information using a second set of filters selected to detect repeaters, thereby providing a second set of defects per slice, and analyzing a plurality of the second sets of defects per slice using a third set of filters selected to detect repeater families, thereby providing a set of repeaters per wafer; and a defect map generator combining the set of repeaters per wafer with a plurality of the first sets of defects per slice, thereby generating one or more defect maps indicative of the random defects and/or repeaters.

Also provided, in accordance with at least one embodiment of the present invention, is a computer program product, comprising a computer usable medium having a computer readable program code embodied therein, the computer readable program code adapted to be executed to implement a method for analyzing an object bearing a repeating pattern suffering from random defects which it is desired to find using a first sensitivity and first false alarm rate and from repeater defects which it is desired to find at a second sensitivity higher than the first sensitivity and second false alarm rate, the method comprising performing a single scan of at least a portion of interest within a object; using a first defect detection path to detect a first set of defects in the object thereby to generate a first defect map comprising a first plurality of defect locations; and using a second weaker defect detection path to detect a second set of defects in the object thereby to generate a second defect map comprising a second plurality of defect locations and generating a specific map by extracting a specific class of defects from the second set of defects, thereby to find on the object, defects not falling within the specific class, using only a single scan and using the first sensitivity, and also to find on the object, defects falling within the specific class, using the same scan but using the second sensitivity.

Further provided, in accordance with at least one embodiment of the present invention, is a computer program product, comprising a computer usable medium having a computer readable program code embodied therein, the computer readable program code adapted to be executed to implement a method for detecting random defects and repeaters accommodated on a wafer, the method comprising performing defect detection on slice information provided by scanning a plurality of wafer slices; analyzing the defect information using a first set of filters selected to detect random defects, thereby generating a first set of defects per slice, and analyzing the defect information using a second set of filters selected to detect repeaters, thereby providing a second set of defects per slice; analyzing a plurality of the second sets of defects per slice using a third set of filters selected to detect repeater families, thereby providing a set of repeaters per wafer; and optionally combining the set of repeaters per wafer with a plurality of the first sets of defects per slice, thereby generating one or more defect maps indicative of the random defects and/or repeaters.

Also provided is a computer program product, comprising a computer usable medium or computer readable storage medium, typically tangible, having a computer readable program code embodied therein, the computer readable program code adapted to be executed to implement any or all of the methods shown and described herein. It is appreciated that any or all of the computational steps shown and described herein may be computer-implemented. The operations in accordance with the teachings herein may be performed by a computer specially constructed for the desired purposes or by a general purpose computer specially configured for the desired purpose by a computer program stored in a computer readable storage medium.

Any suitable processor, display and input means may be used to process, display e.g. on a computer screen or other computer output device, store, and accept information such as information used by or generated by any of the methods and apparatus shown and described herein; the above processor, display and input means including computer programs, in accordance with some or all of the embodiments of the present invention. Any or all functionalities of the invention shown and described herein may be performed by a conventional personal computer processor, workstation or other programmable device or computer or electronic computing device, either general-purpose or specifically constructed, used for processing; a computer display screen and/or printer and/or speaker for displaying; machine-readable memory such as optical disks, CDROMs, magnetic-optical discs or other discs; RAMs, ROMs, EPROMs, EEPROMs, magnetic or optical or other cards, for storing, and keyboard or mouse for accepting. The term "process" as used above is intended to include any type of computation or manipulation or transformation of data represented as physical, e.g. electronic, phenomena which may occur or reside e.g. within registers and/or memories of a computer.

The above devices may communicate via any conventional wired or wireless digital communication means, e.g. via a wired or cellular telephone network or a computer network such as the Internet.

The apparatus of the present invention may include, according to certain embodiments of the invention, machine readable memory containing or otherwise storing a program of instructions which, when executed by the machine, implements some or all of the apparatus, methods, features and functionalities of the invention shown and described herein. Alternatively or in addition, the apparatus of the present invention may include, according to certain embodiments of the invention, a program as above which may be written in any conventional programming language, and optionally a machine for executing the program such as but not limited to a general purpose computer which may optionally be configured or activated in accordance with the teachings of the present invention. Any of the teachings incorporated herein may wherever suitable operate on signals representative of physical objects or substances.

The embodiments referred to above, and other embodiments, are described in detail in the next section.

Any trademark occurring in the text or drawings is the property of its owner and occurs herein merely to explain or illustrate one example of how an embodiment of the invention may be implemented.

Unless specifically stated otherwise, as apparent from the following discussions, it is appreciated that throughout the specification discussions, utilizing terms such as, "processing", "computing", "estimating", "selecting", "ranking", "grading", "calculating", "determining", "generating", "reassessing", "classifying", "generating", "producing", "stereo-matching", "registering", "detecting", "associating", "superimposing", "obtaining" or the like, refer to the action and/or processes of a computer or computing system, or processor or similar electronic computing device, that manipulate and/or transform data represented as physical, such as electronic, quantities within the computing system's registers and/or memories, into other data similarly represented as physical quantities within the computing system's memories, registers or other such information storage, transmission or display devices. The term "computer" should be broadly construed to cover any kind of electronic device with data processing capabilities, including, by way of non-limiting example, personal computers, servers, computing system, communication devices, processors (e.g. digital signal processor (DSP), microcontrollers, field programmable gate array (FPGA), application specific integrated circuit (ASIC), etc.) and other electronic computing devices.

The present invention may be described, merely for clarity, in terms of terminology specific to particular programming languages, operating systems, browsers, system versions, individual products, and the like. It will be appreciated that this terminology is intended to convey general principles of operation clearly and briefly, by way of example, and is not intended to limit the scope of the invention to any particular programming language, operating system, browser, system version, or individual product.

BRIEF DESCRIPTION OF THE DRAWINGS

Certain embodiments of the present invention are illustrated in the following drawings; dotted lines are used to indicate optional blocks within the illustrated embodiments and more generally, any component may be removed or provided depending on demands of specific applications.

DETAILED DESCRIPTION OF CERTAIN EMBODIMENTS

The following acronyms are used herein:
A. IOD—image on demand
B. OTF—on the fly images
C. C2C—Cell 2 Cell detection, for which a purifier as described herein may be employed, even in fields including 2 dies in the direction of D2D detection.
D. V/G, V-G: Volume grade filter, or a functionality which filters out defects based on the volume and/or grade thereof.
E. BB—bounding box
F. AR—aspect ratio
G. IP—image processor
H. CR—capture rate
I. RBP—repeater below post
J. NF—nuisance filter
K. ADI (gate ADI layer)—"after-develop inspect", namely a layer in semiconductor processing)
L. STI—short trench isolation
M. TPT—throughput
N. SR—search radius for repeater analysis. Two defects that are within this distance in field coordinates of each other may be either deemed to belong to the same repeater family or to comprise a pair of non-repeaters.
O. IP—image processor.

The following terms may be construed either in accordance with any definition thereof appearing in the prior art literature or in accordance with the specification, or as follows:
A. Random defects: used interchangeably with "non-repeating defects". In fact, defects which are not repeaters are not necessarily random and therefore, references to random defects herein may be taken to include all defects which are not repeater defects.
B. Die: a chip precursor. Typically a single wafer includes a multiplicity of repeating patterns each of which matures into (is diced into) an independent electronic product such as a computer chip.
C. Field: a group of proximal dies which are patterned together during the fabrication process. For example, in conventional step-and-scan lithography, a mask in a first position relative to the wafer-in-process patterns a first field during a first step; during a second step, the mask is moved to a second position relative to the wafer-in-process and patterns a second field after which it is moved to a third position and so forth. A wafer may include several fields, such as 20 fields, each including several dies, such as 2×1, 2×3, 3×3, or 4×4 dies. The wafer is scanned typically slice by slice. Defect detection may be carried out in die-to-die mode, in cell-to-cell mode, and in die-to-database mode.
D. Repeater defect: a defect characterizing a field and resulting from a group patterning process such as the above described step-and-scan lithography process. An example of such a defect is a haze defect caused by haze at a particular location in a lithography mask. Defects which repeat themselves at a fixed position within several dies which are not alike in their position within their respective fields, are not repeater defects because they characterize dies and not fields; such defects are termed herein die-level systematic defects. Typically, repeater defects, then, occur in a specific die in a field (and not, systematically, at dies other than the specific die) at a fixed position therewith, over several fields.
E. Defect location: a point, typically expressed in microns and typically representing the location of the center of mass (or other representative location within a defect) relative to the field in which the defect occurs.
F. Bin: an individual cell in a 2 dimensional histogram of x and y field locations. Each bin is a rectangle, determined by minimal and maximal x values and minimal and maximal y values, and operative to store defects whose coordinates fall within the field locations defined by the x and y values and which have distinct field ID's. The bin size is described herein as being ⅕ of the search radius, however, it is appreciated that any other suitable fraction may be employed.
G. Histogram Bin Count: The number of defects in a bin occurring in distinct fields.
H. Bin cluster: A cluster of bins in a histogram
I. Repeater Family or "family": the set of all defects which contributed to a particular cluster, or all defects whose locations fall within the bins of a single bin cluster. Each bin cluster is therefore associated with a single family of defects.
J. X-extent of a family: distance, along the x axis, between the pair of relevant defects in the family which are most widely separated along the x axis.
K. Y-extent of a family: distance, along the y axis, between the pair of relevant defects in the family which are most widely separated along the y axis.
L. Candidate defect=a set of proximal pixels which has been identified by the image processor (scan and common detection unit) as possibly comprising a defect
M. Candidate repeater defect—a candidate defect which has been identified, e.g. by a repeater analysis functionality, as possibly being a repeater defect
N. Appearances: of a repeater family in a bin—including all defects that fall within the bin
O. Occurrences: of a repeater family in a bin cluster—refers to defects that belong to the bin cluster, but to different fields. Also termed herein "#-of-repetitions" hence refers to the number of fields in which a defect/defects were detected rather than to the number of defects.

Certain embodiments of the present invention provide a system for high sensitivity repeater detection in wafer inspection. Repeater analysis on inspection maps is a known method for finding defects which appear in the same location in many "fields". Repeater defects are systematic defects which appear at specific locations in the field. Such defects have a variety of sources: field repeaters are often associated with mask problems, which may for example be due to haze on the mask. Systematic die-level defects, in contrast, are often associated with a marginal process. As indicated, in conventional systems, repeater analysis is carried out on the final result of wafer inspection (e.g. on a defect map) in order to separate repeaters from random defects.

According to certain embodiments, haze defects are detected at much higher sensitivity than nominal inspection sensitivity for random defects. Specifically, repeater defects may be detected at a sensitivity which is up to orders of magnitude higher than the inspection sensitivity in the same inspection scan. Enhanced purifying capabilities for filtering false repeaters may be employed. High-sensitivity haze monitoring may be performed on inspected wafers. Typically, throughput of an inspection recipe for random defects is not adversely affected. Inspection images of repeaters may be available as output, also typically without loss of throughput.

Figure 1A:
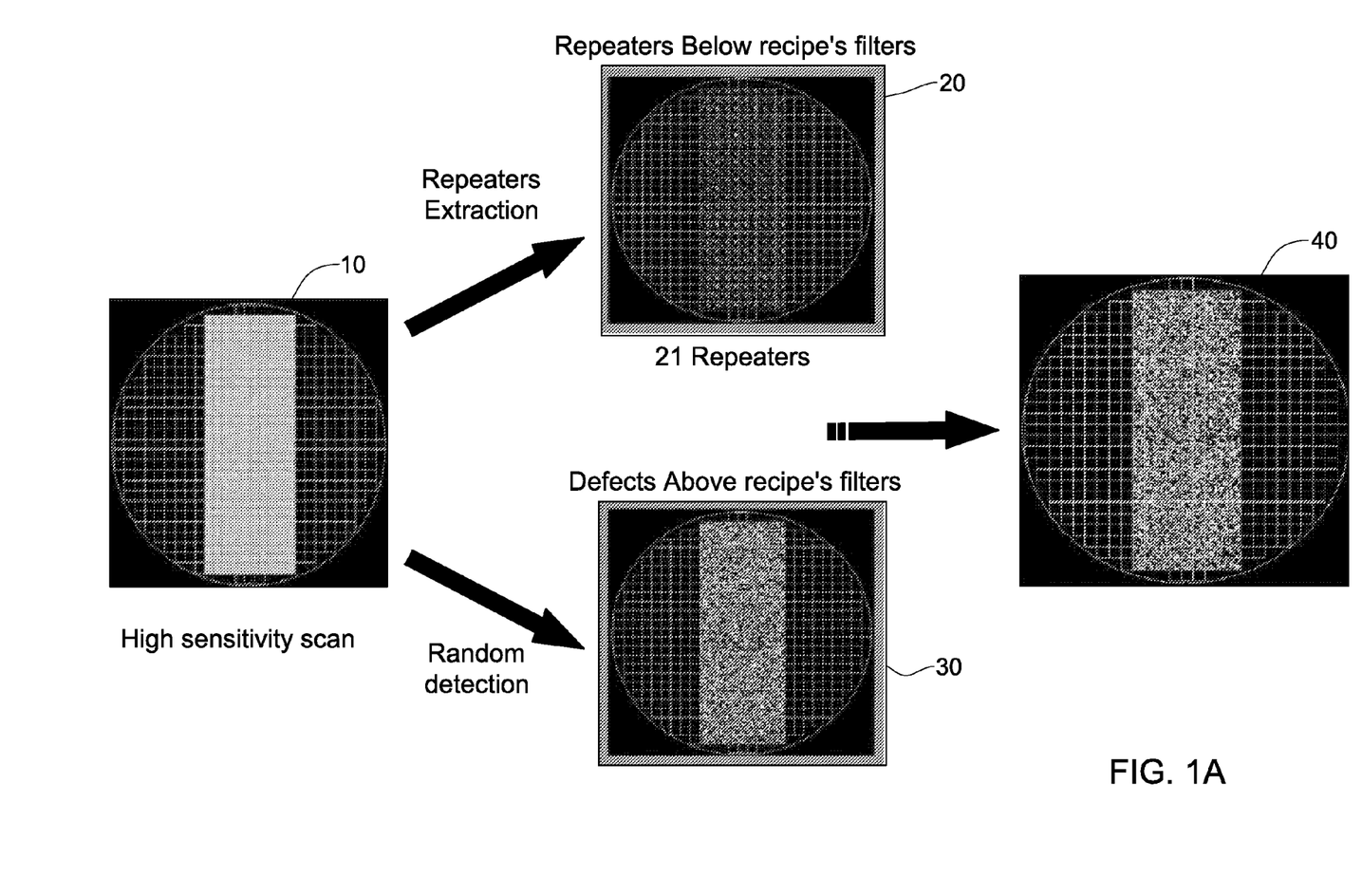
FIG. 1A is a simplified diagram of a defect detection method that increases sensitivity for repeater defects and which monitors for random defects and provides high sensitivity detection for systematic defects, such as haze defects, based on but a single scan.

FIG. 1A is a simplified diagram of a defect detection system that increases sensitivity for repeater defects and which monitors for random defects and provides high sensitivity detection for systematic defects, such as haze defects, based on but a single scan.

As shown, a high sensitivity scan 10 is provided, from which, in a first path, random detection is performed, thereby to generate a map of defects 30 above a given recipe's filters, such as 7942 random defects in the illustrated example. In a second path, repeaters are extracted, thereby to generate a map 20 of repeaters below recipe's filters numbering 21 repeaters in the illustrated example. The two maps 20, 30 are combined or merged to generate a unified map 40 of random defects and repeaters which are extracted below the recipe's filters.

Figure 1B:
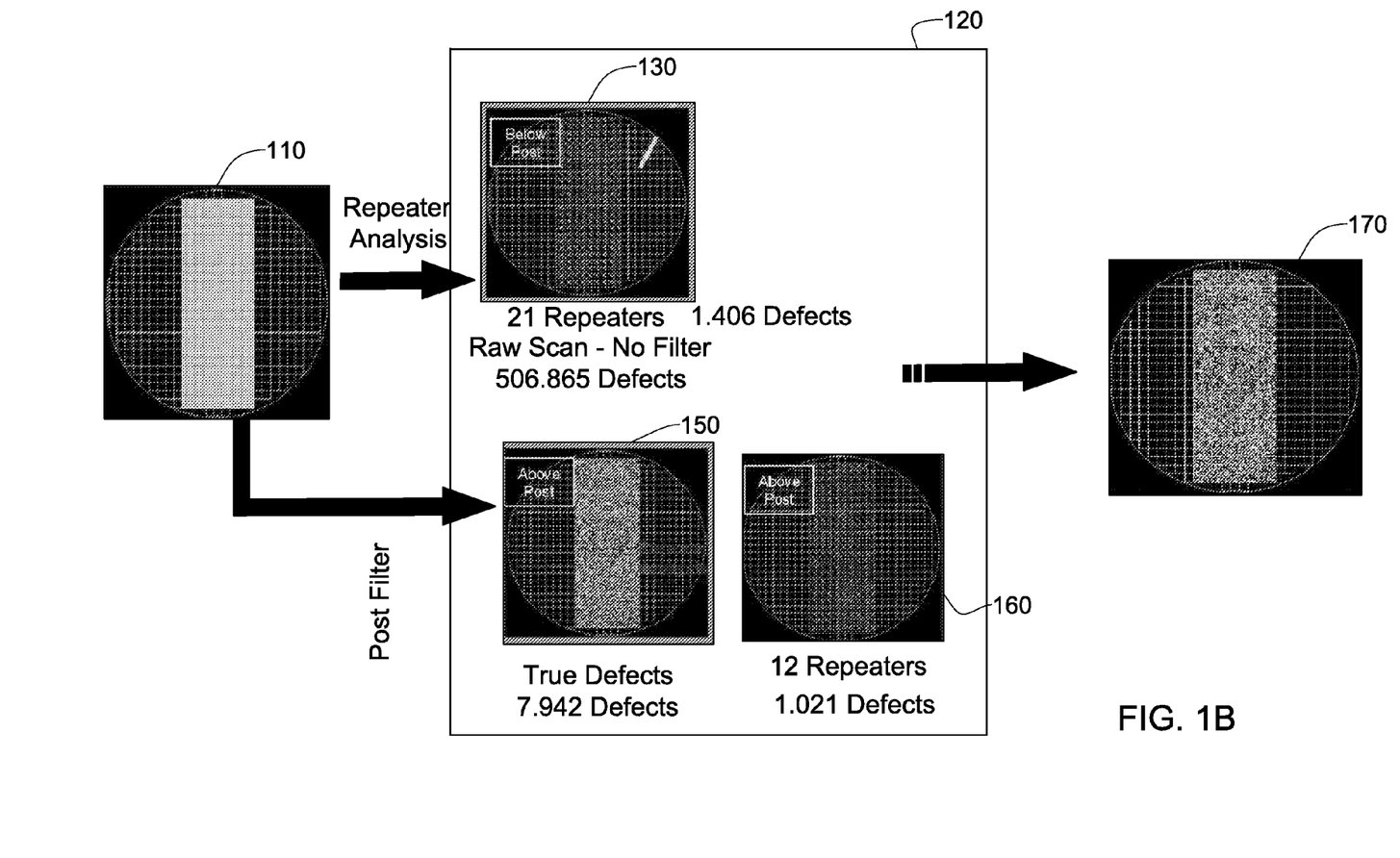
FIG. 1B is a simplified diagram of a defect detection method with 2 parallel detection paths which generates on-the-fly scanned images of repeaters, while scanning.

FIG. 1B is a simplified diagram of a defect detection system 120 with 2 parallel detection paths which generates on-the-fly scanned images, while scanning. As shown, an input 110 undergoes repeater analysis (in one detection path termed herein the "repeater path") and post-filtering (in another detection path termed herein the "inspection path"). The repeater analysis output 130 includes 21 repeater familiess (1406 defects) in the illustrated example. Using a raw scan with no filters, 506,865 defects are found in the illustrated embodiment. Output 150 of the post filter path includes 7942 true defects as shown; the other output 160 of the post filter path includes 12 repeater families (1021 defects). The final output 170 includes all 21 repeater families; from among the total defects only 6332 are seen to be truly random in the illustrated example. It is appreciated, then, that the additional repeater path is valuable in finding new families of repeaters and/or in finding more members within families of repeaters which are known from the inspection path.

Figure 1C:
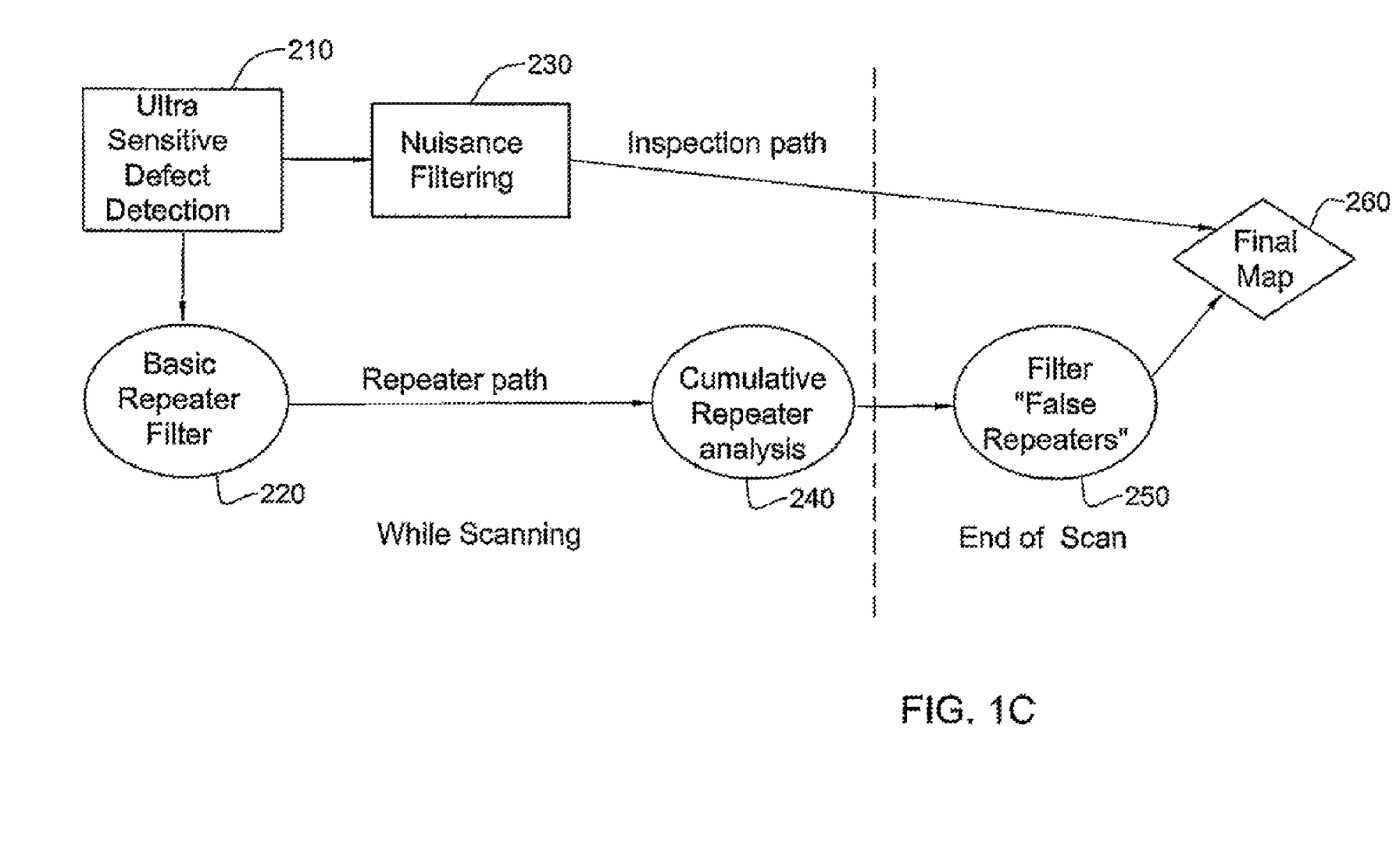
FIG. 1C shows an example defect detection system architecture in accordance with certain embodiments of the present invention, which is suitable for performing the methods of FIGS. 1A and 1B.

FIG. 1C shows an example defect detection system architecture in accordance with certain embodiments of the present invention. As shown, the following functional units are operative while scanning: ultra-sensitive defect detection 210, followed by nuisance filtering 230. A basic repeater filter 220 is applied to the output of ultra-sensitive defect detection 210. Cumulative repeater analysis 240 is performed on the output of the basic repeater filter 220. At the end of the scan, false repeaters are filtered out (module 250). The outputs of nuisance filtering 230 and false repeater filter 250 may be merged to generate a final map 260. Functionalities 210 and 230 form a first channel or path which may be termed the "inspection path" whereas functionalities 220, 240 and 250 form a second channel or path which may be termed the "repeater path". Typically, then, and as shown, repeaters are detected at both the "repeater path" and the "inspection path". "Weak" repeaters that were filtered out by nuisance filtering are not detected at the "inspection path" (only 12 repeaters were detected in the "inspection path" in the illustrated example (160 of FIG. 1B)). Additional repeater detection is performed in the "repeater path" and the results are combined, thus providing highly sensitive repeater detection. According to embodiments of the invention, module 210 is a part of the IP (imager processing) processor, while the modules 220, 230, 240 and 250 are accommodated by a single processor, e.g. "post processor" or by a host computer.

Figure 1D:
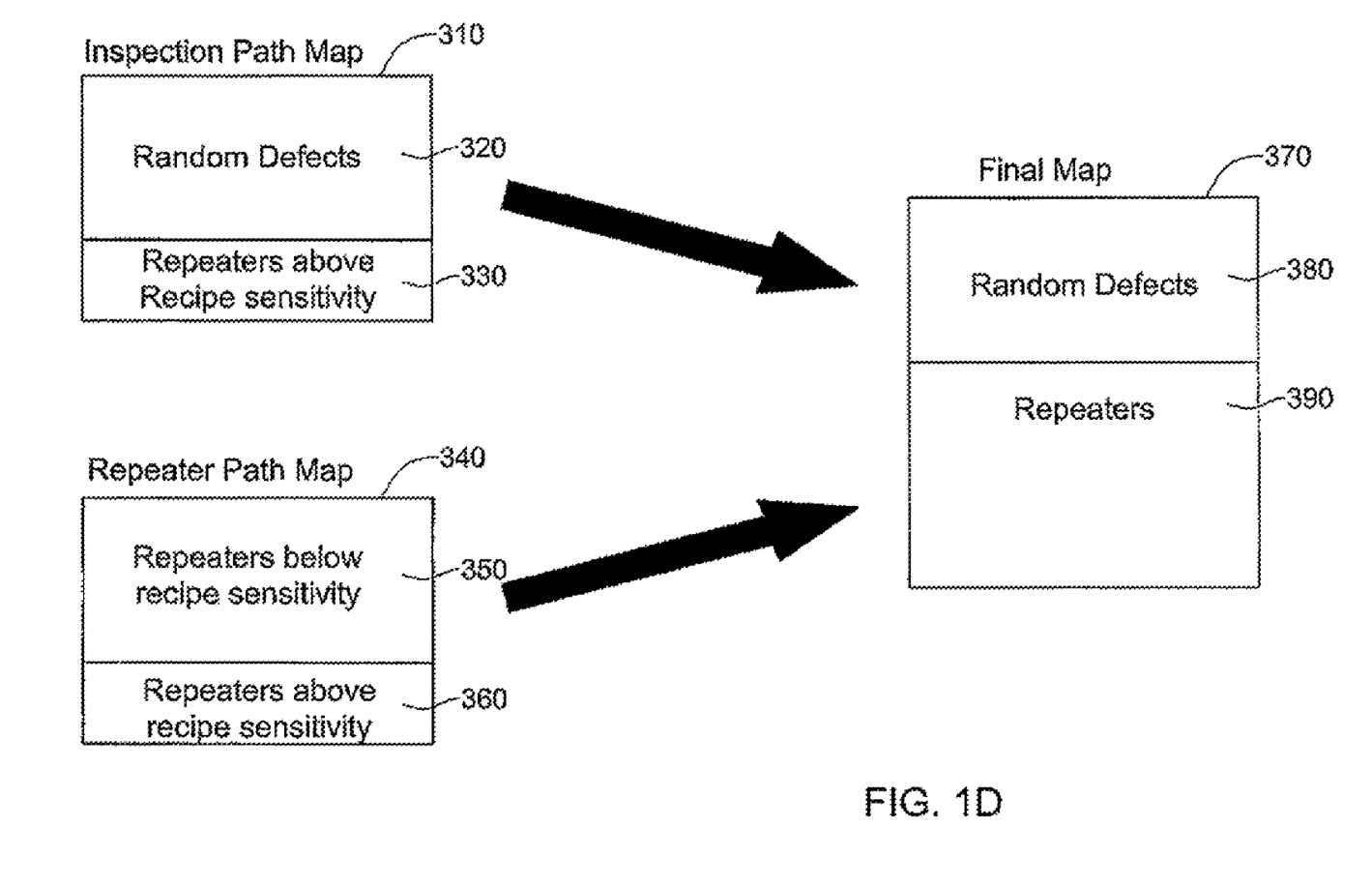
FIG. 1D shows in greater details the merge operation included in the methods of FIGS. 1A and 1B.

FIG. 1D shows in greater details the merge operation included in the methods of FIGS. 1A and 1B. As shown, an inspection path map 310 may be generated which includes random defects 320 and repeaters above recipe sensitivity 330. Similarly, a repeater path map 340 may be generated which includes repeaters below recipe sensitivity 350 and also repeaters above recipe sensitivity 360. The two maps 310 and 340 corresponding to the two paths or channels in FIGS. 1A and/or 1B respectively may be combined into a final map 370 including random defects 380 and repeaters 390.

Figure 2:
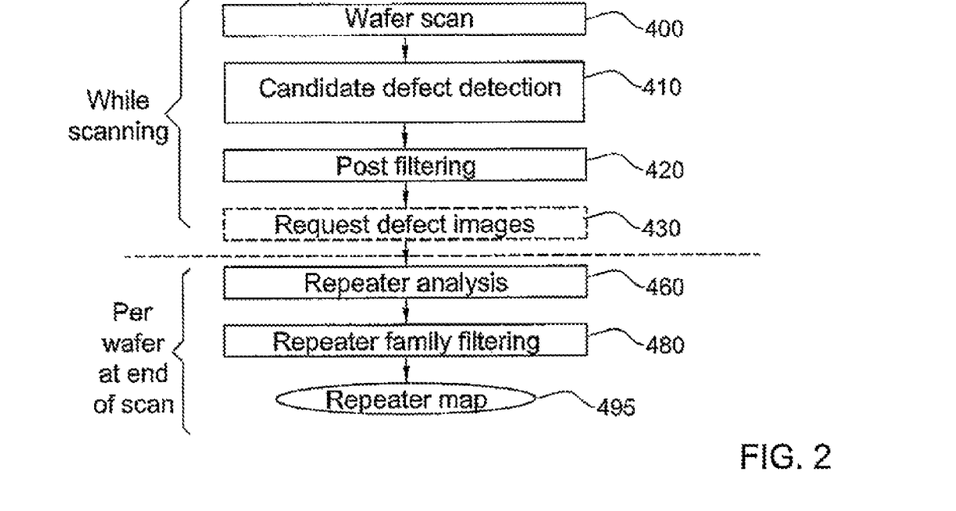
FIG. 2 is a simplified prior art flowchart illustration of a conventional, one-path defect detection method.

FIG. 2 is a simplified prior art flowchart illustration of a conventional defect detection method.

Figure 3:
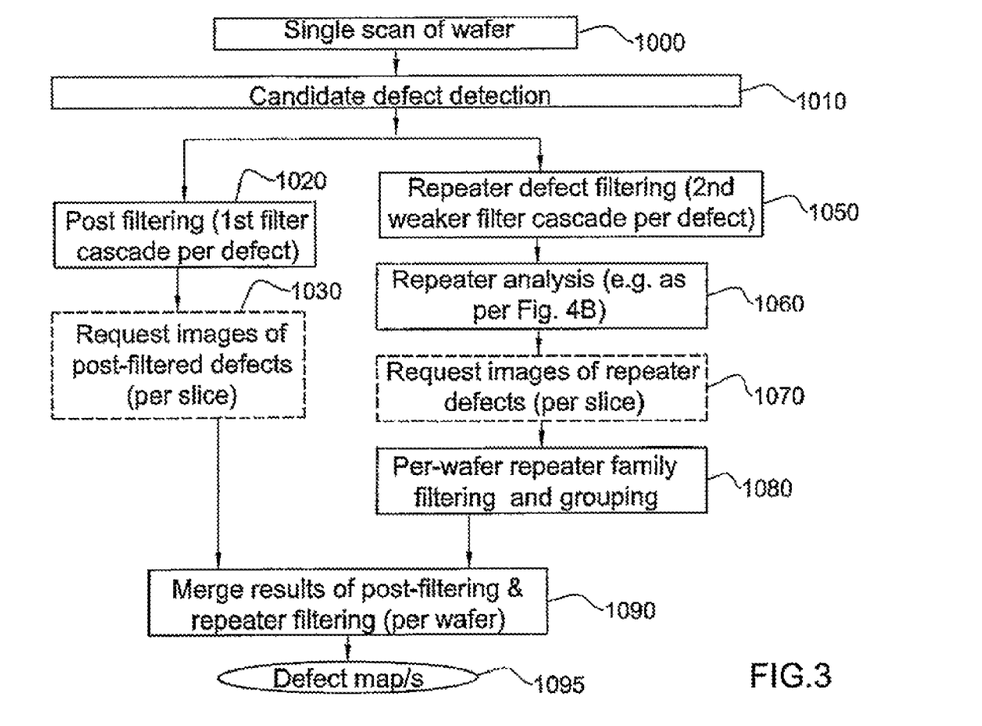
FIG. 3 is a simplified flowchart illustration of a dual path defect detection method operative in accordance with certain embodiments of the present invention, which is suitable for incorporation in a computerized inspection tool for inspection of microscopic patterns, such as but not limited to inspection tools operative to scan and image wafers.

FIG. 3 is a simplified flowchart illustration of a dual path defect detection method according to an embodiment of the invention, including a first sensitivity path or channel using at least one "post filter" (post-processing filter operating on scanned information generated by an image processor) for detecting defects other than repeaters (although some repeaters may be detected as well) and a second sensitivity path or channel for detecting repeaters using at least one repeater filter, thereby to provide a list of "above post defects" that survived all post filters used in the first channel and a list of "repeater defects" that survived all repeater filters used in the second channel although not the post filters used in the first channel; these lists may be merged although repeater defects in the merged list may have some missing defect attributes. According to certain embodiments of the invention, the first sensitivity is lower than the second sensitivity however this is not necessarily so. For example, the first sensitivity filters could be selected to detect repeater defects other than those that could be detected by the second sensitivity filters. For the sake of simplicity, the invention would be described mainly by using the terms "high sensitivity" and "low sensitivity" and it should be noted that the invention is not limited to this example.

As shown in FIG. 3, a wafer or other object (e.g. printed circuits and other objects carried repeatedly printed pattern) is scanned (step 1000) in an image processor. The resulting pixels undergo conventional defect detection (step 1010) for detection of defect candidates. Two separate channels or paths now operate on the output of step 1010, typically in parallel, one for finding defects generally and particularly non-repeater defects ("inspection path") and one specifically for finding repeater defects ("repeater path").

In the inspection path, a post filtering step 1020, performed e.g. by a post-processor, filters out, typically, the majority of the candidates defects found in conventional defect detection step 1010, e.g. on the order of 85%, 90% or 95% thereof (the invention is not limited by the percentage of defects which are filtered at this operation). Images of defects are requested, typically per slice (step 1030). In parallel, in the Repeater path, repeater defect filters filter out a modest percentage of the output of step 1010, perhaps on the order of 10% thereof (step 1050) (the invention is not limited by the percentage of defects which are filtered at this operation). Interim, cumulative repeater analysis 1060 is then performed on the results of step 1050, as scanning is ongoing, e.g. using the method of FIG. 5 or the method of FIG. 4B or similar methods known in the art. According to an embodiment of the invention, this analysis includes the relatively time-consuming operation of constructing field histograms of identified defects. The invention is not limited by the type of repeater analysis which is used. This cumulative repeater analysis 1060 allows images of defects found in the second channel but not in the first channel to be saved (step 1070). At the end of the scan, repeater family grouping and filters are used on the output of the interim repeater analysis 1060, resulting in a rapidly generated list of repeater defects. The list of repeater defects can be merged (step 1090) with the general list of defects emerging from the first defect detection channel to form a map or maps 1095 of any desired logical combination of defects found in the two channels.

According to certain methods known in the art and according to an embodiment of the invention, the IP processor saves a plurality of images of locations associated with defect candidates. These images are saved temporarily until a decision is made with respect to the defect candidate (e.g. at step 420 of FIG. 2, or according to an embodiment of the invention, at steps 1020 and 1060 of FIG. 3): if this candidate is classified as a defect, than a request is generated and the respective image is saved for future use. If the candidate is filtered out, the image is deleted.

It is appreciated that the scan may be performed in any suitable order over the portion of interest. For example, the first slice of the wafer may comprise the first few lines of pixels representing the wafer or portion of interest therewithin, the second slice may comprise the next few adjacent lines, and so forth, until all lines (rows or columns) of interest have been scanned. Alternatively, a "sweeping" scanning mode may be employed in which the first slice of the wafer may comprise the first few lines of pixels within the first line of fields in the wafer, the second slice of the wafer may comprise the same few lines of pixels within the second line of fields in the wafer, and so forth, until all lines of interest within all line of fields have been scanned. It is appreciated that many other modes of and orders of scanning may be employed.

Typically, an inspection recipe filters out suspicious pixels in several stages. The final filters are applied by the post processor on defects. At the end of an inspection scan, repeaters can be automatically identified from the set of surviving defects. However, in prior art systems and methods, "weak" repeaters that were filtered out by the post filters are lost forever. In contrast, according to certain embodiments of the present invention, weak repeaters can be resurrected without changing the sensitivity of the inspection scan for non-repeating defects. This feature is termed herein the "Repeaters from Noise" or "Repeaters below Post" feature.

The output of the analysis carried out on the candidate defects (e.g. steps 1020 to 1080 carried out by e.g. the post processor) typically comprises one, some or all of the following outputs:

A. Defect map: A list of defects with their locations. A map could be generated by the end of step 1020 and/or 1080 and/or 1090. According to an embodiment of the invention, the maps generated by steps 1020 and 1080 are merged at the end of the scan. The invention is not limited by the manner by which the maps generated by steps 1020 and 1080 are merged.

B. Attributes of Defects: Along with the defects, attributes of the defects may be saved.

C. Images of Defect: A set of at least one image can be associated with each defect in the defect map. These images are obtained on demand by requests sent at the end of each slice to the IP processor. It is appreciated that the images may be associated with more than one detector and/or more than one reference images of, say, a neighboring die (in D2D detection).

D. Class: Classifications of defects based on some of its attributes, for example "scratch", "small particle", "bridge".

Following prior art methods such as illustrated in FIG. 2, only images of defects above the post filters are available. As illustrated in FIG. 3, in order to obtain images of repeaters below the post, the potential repeaters must be identified and merged with the "above post" list of defects at the end of each slice. The repeater analysis is typically performed, in part, cumulatively during the scan, so as to best facilitate the image-on-demand feature.

In the method of FIG. 3, repeaters below the post are reported, along with suitable attributes and along with an associated image. According to methods known in the art, the IP alarms are clustered to defect candidates (step 1010) and then processed as described herein.

Basic Post Filter for Repeaters: Referring now to step 1050 in FIG. 3, filters such as grade volume filters (by type) or other filters known in the art (other attributes), are applied to all the defect candidates. The thresholds are either predefined or set by the user. This step is performed in order to set a maximal sensitivity limit on repeaters, thus better discriminating between true and false repeaters.

Figure 4A:
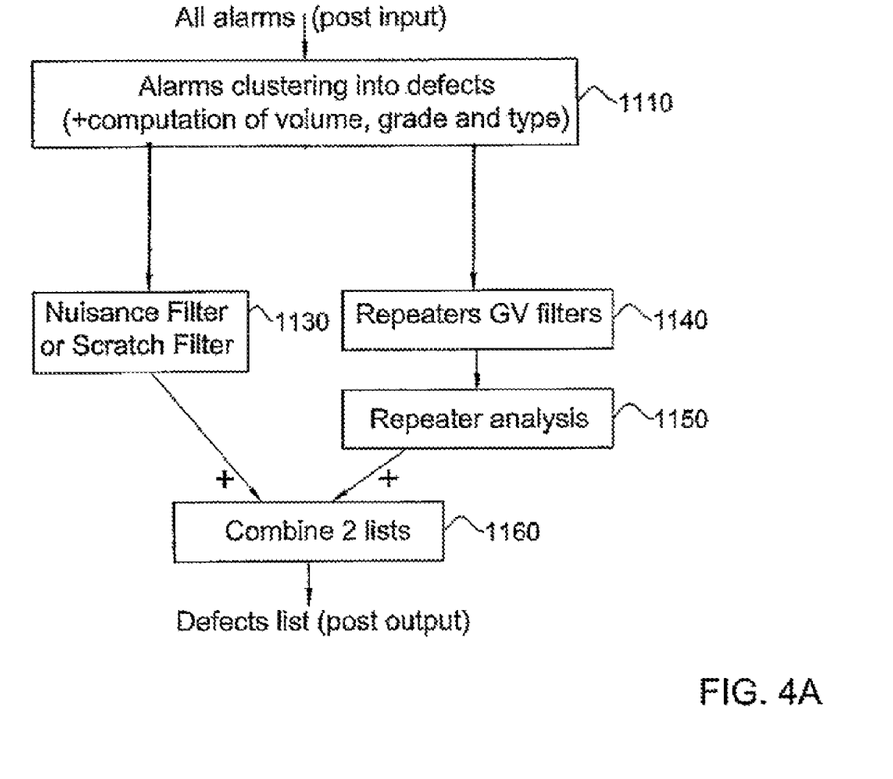
FIG. 4A is a flow diagram of one possible implementation of the method of FIG. 3.
Figure 4B:
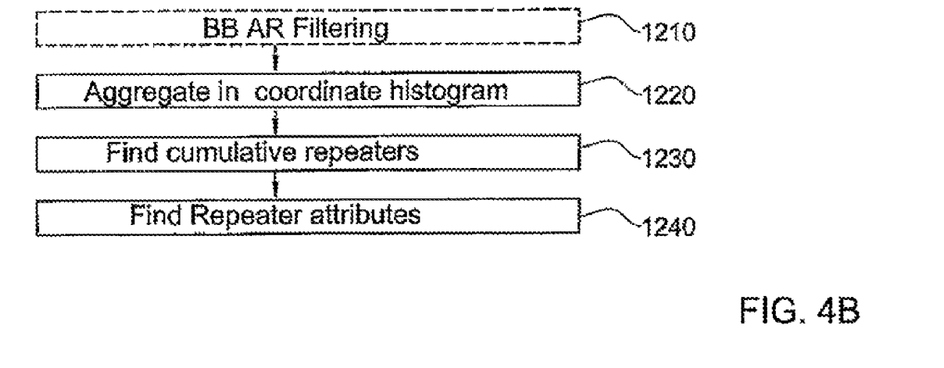
FIG. 4B is one possible flow diagram suitable for implementing the repeater analysis operation in FIG. 4A in accordance with certain embodiments of the present invention.

FIG. 4A is a flow diagram of one possible implementation of the method of FIG. 3. According to an embodiment of the invention, all of the operations of FIG. 4A are carried out by a single computer, e.g. a post processor or a host computer. According to other embodiments, certain operations such as operation 1110 are carried out by the IP processor. FIG. 4B is one possible flow diagram suitable for implementing repeater analysis operation 1150 in FIG. 4A.

BB-AR (Bounding Box-Aspect Ratio) filtering is suitable for detecting repeater defects and may be included as optional operation 1210 of FIG. 4B or may be included in operation 1050 of FIG. 3. The attribute BB-AR (Bounding-Box Aspect-Ratio) is computed for all defects as follows:

$$BB\_aspect\_ratio = \frac{BB\_short\_axis}{BB\_long\_axis} \qquad \text{(Formula I)}$$

Where BB_long_axis is either the width or the height of the bounding box—the longer one of the two, and BB_short axis is the shorter one.

The attribute is used for filtering all defects that comply with:

$$BB\ aspect\ ratio < min\_BB\_aspect\_ratio \qquad \text{(Formula II)}$$

Step 1220 comprises aggregation in a histogram as described in detail herein. Step 1230 comprises identifying cumulative repeaters and generating a potential repeaters list accordingly. Step 1240 of FIG. 4B comprises estimating repeater family attributes on-the-fly.

Referring again to FIG. 3, the conventional detection of step 1010 may use detection filters and operators known in the art such as but not limited to one or more of the following: Nuisance filter, GV (Grade Volume) filter or any other defect level filter.

The invention is not limited by the specific manner by which the repeater analysis operation is implemented. A suitable method for repeater analysis by histogram construction useful for implementing step 1060 of FIG. 3 is now described and illustrated in FIG. 5.

Figure 5:
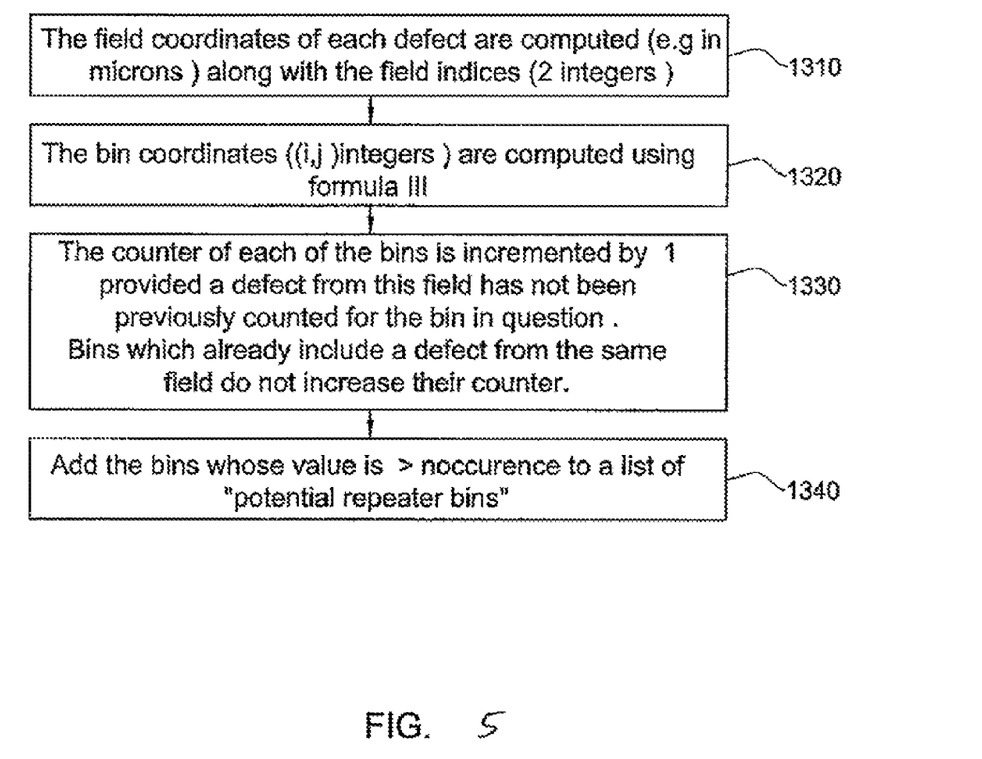
FIG. 5 is a simplified flowchart illustration of a method for performing the repeater analysis step of FIG. 3.

A high resolution coordinate location histogram is defined in memory for all the non-filtered defects that passed the basic post filter of the previous section. The histogram resolution is set to equal a fraction of search_window_x in x-dimension and the same fraction of search_window_y in y-dimension, the extent being the Field size.

From the histogram, once constructed, D2D repetitions and F2F repetitions are extracted on the fly as follows. In addition, modes of identifying repeaters with identical wafer x-coordinate (y-only) or identical y-coordinate (x-only) are also supported.

(1) For each defect, compute the bin $\{i_0, j_0\}$ to which it belongs as follows:

$$\begin{cases} i_0 = (F_x - 1)L_x + \min\left(\left\lfloor \frac{xdie}{bin\_sz\_x} \right\rfloor, L_x - 1\right) + 1 \\ j_0 = (F_y - 1)L_y + \min\left(\left\lfloor \frac{ydie}{bin\_sz\_y} \right\rfloor, L_y - 1\right) + 1 \end{cases} \quad \text{(Formula III)}$$

where $L_x$ and $L_y$ (integers) are the number of bins in a die along the x and y-axis respectively. $F_x$ and $F_y$ are the x and y die indices respectively of the defect's die within the field (the lower left die in the field is indexed as (1,1)).

For each defect placed in the histogram, the relevant histogram counters must be updated. The field-list of the bin may include the current field. The histogram counter of each of these bins may be raised by 1 in case the field-list of the bin does not contain the current field yet.

If the following condition (according to an embodiment of the invention, the parameter $N_{occur}$, represents a predetermined or dynamic threshold number of occurrences of a defect at a given field location) holds for any of the counters in step 1 that were increased:

$$N(i,j) \geq N_{occur} \quad \text{(Formula IV)}$$

(2) add the location (i,j) to the list of "Potential Repeaters", if it is not there already. For x-only (y-only) analysis mode, a potential repeater also has associated with it a y die index (x die index). If the analysis mode is x-only (y-only), then the sum is only over defects in the histogram bins with the same y-die index (x-die index). In x-only analysis mode, the number of 2D histograms is the number of field rows and for each histogram only defects from that field row can contribute. In y-only analysis mode, the number of 2D histograms is the number of field columns and for each histogram only defects from that field column can contribute.

At the end of the scan, this accumulated list is grouped using some clustering method such as chain clustering with gaps of 1 pixel or more. This results in a list of potential repeater families.

Once grouped, the repeater families are filtered according to their number of occurrences. For Capture Rate mode (see below), the threshold $N_{occur}$ (also termed herein Noccurrence) is computed using the scan plan and the field size as follows:

A. For each die in the field, compute fields_in_scan_num-$_{die}$, which is the number of times the die of the field repeats in the scan-plan.

B. Then for each die in the field, compute its $N_{occur}$ threshold using:

$$N_{occur}(die) = \lfloor num\_fields\_in\_scan_{die} * CR\_threshold \rfloor \quad \text{(Formula V)}$$

For x-only mode, $$N_{occur}(die) = \lfloor num\_fields\_in\_row * CR\_threshold \rfloor \quad \text{(Formula VI)}$$

num_fields_in_row$_{die, row}$ is computed for each die in the field per row, at the beginning of the scan, and is the number of repetitions of the die in the field along the specific row. Similarly, for y-only mode, $$N_{occur}(die) = \lfloor num\_fields\_in\_column_{die} * CR\_threshold \rfloor \quad \text{(Formula VII)}$$

The terms used above may be understood conventionally or as follows:

A. Scan Plan: Geographical areas of the wafer which is scanned for defects
B. Field Size: Physical Size of rectangular field.
C. Capture Rate Mode: Rather than setting a fixed value for Noccurrence the number is computed based on an input percentage of the number of fields scanned (computed from scan plan/field size).

IOD (image on demand) Requests are made in steps 1030 and 1070 of FIG. 3. At the end of each slice, images are requested from the IP processor. The images that are requested may be a subset of the defects that passed (not filtered out by) the post filters. According to prior art methods (e.g. as illustrated in FIG. 2), there is no special consideration of repeaters since these are identified only at the end of the scan. However, obtaining images on repeater representatives below the post (that is, those which would have been filtered out by post filtering 420 of FIG. 2) may also be achieved by carrying out the repeater analysis cumulatively per slice (FIG. 3, step 160) and requesting the images based on an estimate of whether they will turn out to be repeaters. These estimates are only carried out if both IODs (step 1030 and 1070 in FIG. 3) are operating and repeaters are not "filtered".

Each time a new defect is added to the histogram, a decision is made, typically just afterward, as to whether to add its location to the list of requests for the current slice. Images may be requested if a logical combination of the following criteria holds, e.g. if all of the following criteria (I)-(III) hold:

A. Criteria I—New Field has been added: The defect increased any of the 1, 9 or 25 (say) field histogram counters in its (say) 1×1, 3×3 or 5×5 neighbourhood respectively, as described above.

B. Criteria II—Field Repetitions are sufficient for image request: The number of field repetitions obeys:

$$N(i,j) > N_{request} \quad \text{(Formula VIII)}$$

where (i,j) is any one of the bins which obeys criterion (i) above, and $N_{request}$ is a predetermined or dynamic parameter representing a threshold number of occurrences for requesting images:

C. Criteria III—"Purifier"<Scan set purifier threshold: For each defect, the purifier attribute estimate is carried out, where i__0 is used interchangeably with index I and j__0 is used interchangeably with index j:

$$\text{Purifier}(i_0, j_0) = \frac{D2D(i_0, j_0) - F2F(i_0, j_0)}{F2F(i_0, j_0)} \quad \text{(Formula X)}$$

where $F2F(i_0, j_0)$ is the number of fields the repeater in question appears in, and it equals $N(i_0, j_0)$. And $D2D(i_0, j_o)$ is the number of dies the repeater in question appears in; it is computed from the field histogram as follows:

$$D2D(i_0, j_0) = \sum_{D \in Field} F2F(i_0^{(D)}, j_0^{(D)}) \quad \text{(Formula XI)}$$

where $(i_0^{(D)}, j_0^{(D)})$ is the bin in the histogram which corresponds to the same die location as $(i_0, j_0)$ but belongs to die D in the field. The summation in Formula XI above is over the number of dies in a field. Note that for field size y equal to 2 dies and D2D detection in y, the summation in Formula XI above is only over all the dies D in the field except for the one with these same field location in x but differing field location in y. This also holds, mutatis mutandis, for D2D scanning in x and fields of size 2 dies in x-direction.

Each defect that obeys these rules is added to the IOD list. For the first time an image of a potential repeater in this location in the field has been requested, add to the list all the previous locations in the slice in which a defect was detected in the same location in the field.

The invention is not limited by the specific manner by which the repeater family filtering is implemented. A method for performing the repeater family filtering step 1080 of FIG. 3 is now described with reference to FIG. 6. Generally, at the end of scan, the potential repeaters list generated by step 1230 in FIG. 4B is further clustered to obtain the final repeaters locations. The method typically comprises some or all of the following steps, suitably ordered e.g. as illustrated.

Figure 6:
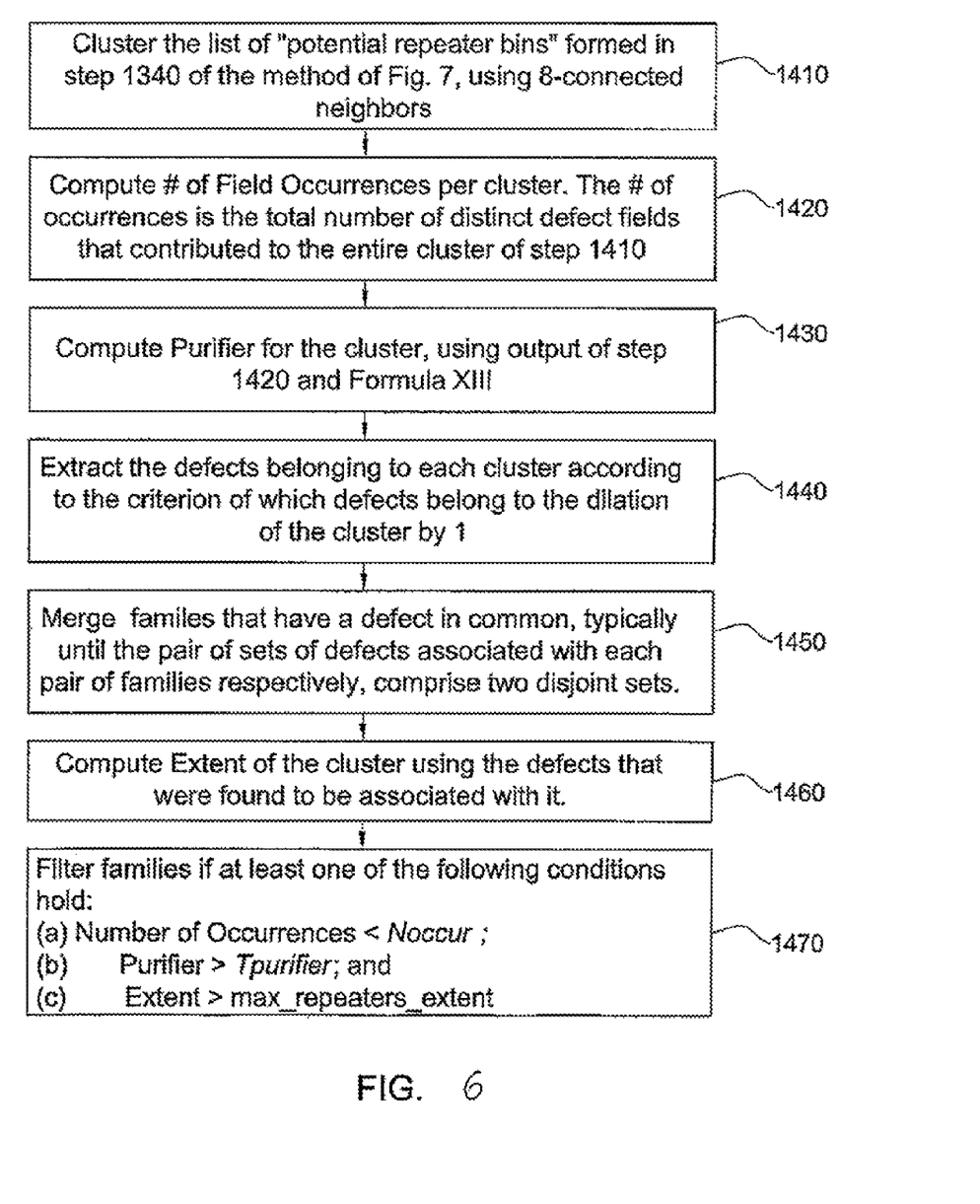
FIG. 6 is a simplified flowchart illustration of a method for performing the repeater family filtering step of FIG. 3.

Step 1410: Cluster the list of "potential repeater bins" formed in step 1340 of the method of FIG. 5, using 8-connected neighbors. In Step 1410, on the list of potential repeaters in field coordinates, connected components are found as follows: all the potential repeater bins are clustered according to e.g. 8-connected neighborhoods (other clustering methods can be used). This means that two potential repeater pixels at locations (x0,y0) and (x1,y1) belong to the same connected component provided the following two criteria hold:

$$\begin{cases} |x_0 - x_1| \le 1 \\ |y_0 - y_1| \le 1 \end{cases} \quad \text{(Formula XII)}$$

Step 1420: Compute number of Field Occurrences per cluster. The number of occurrences is the total number of distinct defect fields that contributed to the entire cluster of step 1410.

Step 1430: Compute "Purifier" for the cluster, using output of step 1420 and Formula XIII Step 1440: Extract the defects belonging to each cluster according to the criterion of which defects belong to the dilation of the cluster by 1, where clustering, also termed connected component analysis and dilation, is known in the art Step 1450: Merge families that have a defect in common, typically until the pair of sets of defects associated with each pair of families respectively, comprise two disjoint sets.

Step 1460: Compute Extent of the cluster using the defects that were found to be associated with it. There can be more than 1 defect per field (even in field size 1×1).

Step 1470: Filter families (a family is the set of all defects which contributed to a particular cluster) if at least one of the following conditions hold: (a) No. of Occurrences<Noccur; (b) Purifier>Tpurifier, and (c) Extent>max_repeaters_extent.

It is appreciated that, for each connected component, the following attributes are computed per repeater family:

A. Number of Occurrences=sum of different fields in the fields-list, of all bins attached to the repeaters cluster (step 1420)

$$\text{Purifier (bin\_cluster)} = \frac{D2D(\text{bin\_cluster}) - F2F(\text{bin\_cluster})}{F2F(\text{bin\_cluster})}, \quad \text{(Formula XIII- step 1430)}$$

where F2F(bin_cluster)=Number_of_occurances(bin_cluster) as computed in step 1420, and $$D2D(\text{bin\_cluster}) = \sum_{D \in Field} F2F(\text{bin\_cluster}^{(D)})$$

where bin_cluster$^{(D)}$ is the cluster of bins in the histogram which corresponds to the same die locations as the current bin-cluster, but belongs to die D in the field.

B. X-extent, Y-extent=step 1460 computes measures of repeater-cluster accuracy which hold the distance between different appearances of the repeater. They are computed after extracting the defects that belong to each repeater family, from the family bins and their neighbors. While extracting the defects, in case one of the defects belongs to more than 1 repeater family, combine the 2 repeater families. In such a case, the number of occurrences may be recomputed i. X-extent is computed as follows:

$$X\text{-extent} = \text{Max}_{d \in relevant\_defects}(\text{cm\_}x(d)) - \text{Min}_{d \in relevant\_defects}(\text{cm\_}x(d)) \quad \text{(Formula XIV)}:$$

where cm_x is the center of mass of the defect, on the x-axis. And the relevant defects are the n defects that are closest to the median center of mass in x of all defects that belong to the relevant repeaters family, $$n = \max(N_{occur}, [\text{extent\_factor}^* \text{num\_of\_defects}])$$

num_of_defects is the number of appearances_of the repeaters family.

ii. Y-extent is computed analogously.

Step 1470: The filters are carried out in the following order:

A. Number of Occurrences<N$_{occur}$ (actual filtering is before clustering)

B. Purifier>T$_{purifier}$

C. Max {x-extent, y-extent}>max_repeaters_extent

A repeater family obeying at least one of the above criteria is filtered. In order to reach as low computation time as possible, the number of occurrences and purifiers are computed before the actual repeater defects are found—when there are only repeaters locations.

Step 1090 in FIG. 3 merges the Defect List generated by the left-hand first defect detection channel with the Repeater List generated by the right-hand second defect detection channel. Generally, at the end of the scan, there are 2 defect lists that must be merged (the usual defects above the post and the repeater defects). A defect may appear in both lists; such a defect is given type "Repeater" rather than its "Above Post" type. The following attributes may be stored for each repeater defect:

A. Type="Repeater"
B. xy location, Grade, Volume, BB
C. Size of a repeater
D. Repeater ID Once a repeater algorithm is operational, various possibilities exist as to which defects to include in the final map, such as but not limited to Repeaters only, Non-Repeaters only and Keep all defects. According to an embodiment of the invention, a merged list is provided. According to other embodiments, a map of repeaters only is provided; a map of defects excluding repeaters could also be provided.

It is appreciated that certain embodiments of the present invention are useful for finding on an object such as but not limited to a wafer, defects which do not fall within a specific class of defects such as but not limited to the class of repeater defects or the class of signature defects, using only a single scan and using a first sensitivity, and also for finding on the object, defects falling within that specific class, using the same scan but using a second sensitivity.

It is appreciated that use of a high sensitivity detection scheme normally results in a high false alarm rate. However, according to certain embodiments of the present invention, the false alarm rate characterizing the set of repeaters extracted is low relative to the high sensitivity used to generate the defect locations from which the repeaters were extracted. It is believed that this is the case because, first, many defects are not repeaters such that the false alarm rate associated with their being identified as defects does not affect the final false alarm rate of the repeaters at all since all such defects are absent from the final set of repeater defects; although the false alarm rate associated with some of them being mis-identified as repeaters could adversely affect the false alarm rate. Second of all, special filters may be used which are particularly suited for identifying repeater filters. Third, repeaters genuinely cluster at their locations because an actual physical process (e.g. a local deterioration of the mask) causes them to occur at those specific locations rather than others.

It is appreciated that terminology such as "mandatory", "required", "need" and "must" refer to implementation choices made within the context of a particular implementation or application described herewithin for clarity and are not intended to be limiting since in an alternative implantation, the same elements might be defined as not mandatory and not required or might even be eliminated altogether.

It is appreciated that software components of the present invention including programs and data may, if desired, be implemented in ROM (read only memory) form including CD-ROMs, EPROMs and EEPROMs, or may be stored in any other suitable computer-readable medium such as but not limited to disks of various kinds, cards of various kinds and RAMs. Components described herein as software may, alternatively, be implemented wholly or partly in hardware, if desired, using conventional techniques. Conversely, components described herein as hardware may, alternatively, be implemented wholly or partly in software, if desired, using conventional techniques.

Included in the scope of the present invention, inter alia, are electromagnetic signals carrying computer-readable instructions for performing any or all of the steps of any of the methods shown and described herein, in any suitable order; machine-readable instructions for performing any or all of the steps of any of the methods shown and described herein, in any suitable order; program storage devices readable by machine, tangibly embodying a program of instructions executable by the machine to perform any or all of the steps of any of the methods shown and described herein, in any suitable order; a computer program product comprising a computer useable medium having computer readable program code, such as executable code, having embodied therein, and/or including computer readable program code for performing, any or all of the steps of any of the methods shown and described herein, in any suitable order; any technical effects brought about by any or all of the steps of any of the methods shown and described herein, when performed in any suitable order; any suitable apparatus or device or combination of such, programmed to perform, alone or in combination, any or all of the steps of any of the methods shown and described herein, in any suitable order; electronic devices each including a processor and a cooperating input device and/or output device and operative to perform in software any steps shown and described herein; information storage devices or physical records, such as disks or hard drives, causing a computer or other device to be configured so as to carry out any or all of the steps of any of the methods shown and described herein, in any suitable order; a program pre-stored e.g. in memory or on an information network such as the Internet, before or after being downloaded, which embodies any or all of the steps of any of the methods shown and described herein, in any suitable order, and the method of uploading or downloading such, and a system including server/s and/or client/s for using such; and hardware which performs any or all of the steps of any of the methods shown and described herein, in any suitable order, either alone or in conjunction with software.

Any computations or other forms of analysis described herein may be performed by a suitable computerized method. Any step described herein may be computer-implemented. The invention shown and described herein may include (a) using a computerized method to identify a solution to any of the problems or for any of the objectives described herein, the solution optionally includes at least one of a decision, an action, a product, a service or any other information described herein that impacts, in a positive manner, a problem or objectives described herein; and (b) outputting the solution.

Features of the present invention which are described in the context of separate embodiments may also be provided in combination in a single embodiment. Conversely, features of the invention, including method steps, which are described for brevity in the context of a single embodiment or in a certain order may be provided separately or in any suitable subcombination or in a different order. "e.g." is used herein in the sense of a specific example which is not intended to be limiting. Devices, apparatus or systems shown coupled in any of the drawings may in fact be integrated into a single platform in certain embodiments or may be coupled via any appropriate wired or wireless coupling.

What is claimed is:

1. A method for analyzing an object bearing a repeating pattern suffering from random defects which it is desired to find using a first sensitivity and first false alarm rate and from repeater defects which it is desired to find at a second sensitivity higher than said first sensitivity and second false alarm rate, the method comprising: performing a single scan of at least a portion of interest within an object; using a first defect detection path to detect a first set of defects in the object thereby to generate a first defect map comprising a first plurality of defect locations; and using a second weaker defect detection path to detect a second set of defects in the object thereby to generate a second defect map comprising a second plurality of defect locations and generating a specific map by extracting a specific class of defects from said second set of defects, thereby to find on said object, defects not falling within said specific class, using only a single scan and using said first sensitivity, and also to find on said object, defects falling within said specific class, using the same scan but using said second sensitivity.

2. A method according to claim 1 wherein said specific map comprises a repeater map and said specific class of defects comprises repeater defects.

3. A method according to claim 1 wherein said first and second paths include first and second filter cascades respectively and wherein said second filter cascade includes at least one filter having a lower threshold than a corresponding filter in said first filter cascade.

4. A method according to claim 2 and also comprising pruning said repeater map to eliminate die-level systematic defects.

5. A method according to claim 4 wherein said pruning is performed after at least a substantial fraction of the portion of interest within the object has been scanned and wherein said pruning comprises retaining as repeater defects, only defect locations, each individual one of which share a field position with a number of other defect locations which number is at least almost as large as the number of defect locations which share a die position with said individual defect location.

6. A method according to claim 5 wherein said substantial fraction of the object comprises the entirety of the object.

7. A method according to claim 1 and also comprising: accumulating information regarding repetition of defects detected by said first detection path as the repetition is encountered and before said scan of said object has been completed; per-slice, evaluating said information including using said information to generate a repeater analysis output and using said repeater analysis output to select for imaging, only a subset of defects detected by said first defect detection path; and per-slice, requesting images only of said subset of defects detected by said first defect detection path.

8. A method according to claim 1 and also comprising merging at least some of said maps thereby to obtain a map of a predetermined logical combination of defects included in said maps.

9. A method according to claim 1 wherein said object comprises a wafer.

10. A method according to claim 7 wherein said accumulating includes accumulating information regarding repetition of defects detected by said first detection path in an individual slice of the object as said slice of said object is being scanned and before scanning of said slice has been completed.

11. A method for detecting random defects and repeaters accommodated on a wafer, the method comprising: performing defect detection on slice information provided by scanning a plurality of wafer slices; analyzing said defect information using a first set of filters selected to detect random defects, thereby generating a first set of defects per slice, and analyzing said defect information using a second set of filters selected to detect repeaters, thereby providing a second set of defects per slice; analyzing a plurality of said second sets of defects per slice using a third set of filters selected to detect repeater families, thereby providing a set of repeaters per wafer; and optionally, combining said set of repeaters per wafer with a plurality of said first sets of defects per slice, thereby generating one or more defect maps indicative of said random defects and/or repeaters.

12. A method according to claim 11 further comprising at least one of: upon generating a first set of defects per slice, initiating a request for images corresponding to defects included in said first set of defects per slice; and upon generating a second set of defects per slice, initiating a request for images corresponding to defects included in said second set of defects per slice, thereby enabling allocation of images associated with defects included in said defect map.

13. A method according to claim 11 wherein said defect detection on slice information includes clustering of alarms included in said slice information into suspected defects by computation of Volume, grade and type.

14. A method according to claim 11 wherein said first set of filters and said second set of filters: have at least one filter in common; have a different number of filters, the second set of filters includes less filters than the first set of filters; and have at least one filter in common and the filter included in the second set of filters is configured with a lower threshold than a corresponding filter in said first set of filters.

15. A method according to claim 11 wherein at least one of said first set of filters and said second set of filters includes at least one of the following filters: Nuisance filter, GV filter, a defect level filter.

16. A method according to claim 11 wherein said third set of filters includes at least one of the following filters: Nuisance filter, GV filter, a defect level filter.

17. A method according to claim 11 wherein combining said set of repeaters per wafer with a plurality of said first sets of defects per slice includes one of the following: selecting defects included in both said set of repeaters per wafer and said plurality of said first sets of defects per slice; selecting defects included at least in said set of repeaters per wafer or said plurality of said first sets of defects per slice; updating attributes associated with defects included in the first or second set with defect information included in the second or first set, respectively.

18. A method according to claim 1 wherein said first and second paths include first and second filter cascades respectively and wherein said second filter cascade includes less filters than said first filter cascade.

19. A system for analyzing an object bearing a repeating pattern suffering from random defects which it is desired to find using a first sensitivity and first false alarm rate and from repeater defects which it is desired to find at a second sensitivity higher than said first sensitivity and second false alarm rate, the system comprising: a scanner performing a single scan of at least a portion of interest within a object; a first detection functionality using a first defect detection path to detect a first set of defects in the object thereby to generate a first defect map comprising a first plurality of defect locations; and a second detection functionality using a second weaker defect detection path to detect a second set of defects in the object thereby to generate a second defect map comprising a second plurality of defect locations and generating a specific map by extracting a specific class of defects from said second set of defects, thereby to find on said object, defects not falling within said specific class, using only a single scan and using said first sensitivity, and also to find on said object, defects falling within said specific class, using the same scan but using said second sensitivity.

20. A system for detecting random defects and repeaters accommodated on a wafer, the system comprising: a defect detector performing defect detection on slice information provided by scanning a plurality of wafer slices; a defect information analyzer analyzing said defect information using a first set of filters selected to detect random defects, thereby generating a first set of defects per slice (1020), analyzing said defect information using a second set of filters selected to detect repeaters, thereby providing a second set of defects per slice, and analyzing a plurality of said second sets of defects per slice using a third set of filters selected to detect repeater families, thereby providing a set of repeaters per wafer; and a defect map generator combining said set of repeaters per wafer with a plurality of said first sets of defects per. slice, thereby generating one or more defect maps indicative of said random defects and/or repeaters.

21. A computer program product, comprising a non-transitory computer usable medium having a computer readable program code embodied therein, said computer readable program code adapted to be executed to implement a method for analyzing an object bearing a repeating pattern suffering from random defects which it is desired to find using a first sensitivity and first false alarm rate and from repeater defects which it is desired to find at a second sensitivity higher than said first sensitivity and second false alarm rate, the method comprising: performing a single scan of at least a portion of interest within a object; using a first defect detection path to detect a first set of defects in the object thereby to generate a first defect map comprising a first plurality of defect locations; and using a second weaker defect detection path to detect a second set of defects in the object thereby to generate a second defect map comprising a second plurality of defect locations and generating a specific map by extracting a specific class of defects from said second set of defects, thereby to find on said object, defects not falling within said specific class, using only a single scan and using said first sensitivity, and also to find on said object, defects falling within said specific class, using the same scan but using said second sensitivity.

22. A computer program product, comprising a non-transitory computer usable medium having a computer readable program code embodied therein, said computer readable program code adapted to be executed to implement a method for detecting random defects and repeaters accommodated on a wafer, the method comprising: performing defect detection on slice information provided by scanning a plurality of wafer slices; analyzing said defect information using a first set of filters selected to detect random defects, thereby generating a first set of defects per slice, and analyzing said defect information using a second set of filters selected to detect repeaters, thereby providing a second set of defects per slice; analyzing a plurality of said second sets of defects per slice using a third set of filters selected to detect repeater families, thereby providing a set of repeaters per wafer; and optionally combining said set of repeaters per wafer with a plurality of said first sets of defects per slice, thereby generating one or more defect maps indicative of said random defects and/or repeaters.

* * * * *